United States Patent
Chou et al.

(10) Patent No.: US 9,322,781 B2
(45) Date of Patent: Apr. 26, 2016

(54) METHOD FOR PRODUCING OPTICALLY STIMULATED LUMINESCENE DOSAGE DETECTION CRYSTAL

(71) Applicant: Mitch M. C. Chou, Kaohsiung (TW)

(72) Inventors: Mitch M. C. Chou, Kaohsiung (TW); Chu-An Li, Kaohsiung (TW)

(73) Assignee: Mitch M. C. Chou, Kaohsiung (TW)

( * ) Notice: Subject to any disclaimer, the term of this patent is extended or adjusted under 35 U.S.C. 154(b) by 55 days.

(21) Appl. No.: 14/580,415

(22) Filed: Dec. 23, 2014

(65) Prior Publication Data

US 2015/0198530 A1 Jul. 16, 2015

(51) Int. Cl.
*G01N 21/64* (2006.01)
*C09K 11/65* (2006.01)
*G21K 4/00* (2006.01)

(52) U.S. Cl.
CPC ............. *G01N 21/64* (2013.01); *C09K 11/655* (2013.01); *G01N 2201/061* (2013.01); *G21K 2004/06* (2013.01)

(58) Field of Classification Search
CPC ....................................................... G01N 21/64
See application file for complete search history.

(56) References Cited

U.S. PATENT DOCUMENTS

| | | | |
|---|---|---|---|
| 8,652,358 B2 * | 2/2014 | Okuyama et al. | 252/301.4 F |
| 2003/0218151 A1 * | 11/2003 | Akselrod | 252/301.4 R |
| 2004/0069210 A1 * | 4/2004 | Akselrod | 117/13 |

\* cited by examiner

*Primary Examiner* — Nathan T Leong
(74) *Attorney, Agent, or Firm* — Jackson IPG PLLC; Demian K. Jackson

(57) ABSTRACT

A method for producing an optically stimulated luminescene (OSL) dosage detection crystal is disclosed, where an $Al_2O_3$ is first covered with carbon. The carbon atoms are diffused then in vacuum into the $Al_2O_3$ lattices. Then, the oxygen and carbon atoms react with each other in an anneal process under 1 atm. At this time, oxygen and the carbon atoms are enabled to react with each other, and thus C+O result in CO, or $C+O_2$ form $CO_2$, so that oxygen vacancy deficiencies are formed in the $Al_2O_3$ crystal. At this time, a uniformly carbon distributed crystal structure is thus simply obtained.

4 Claims, 1 Drawing Sheet

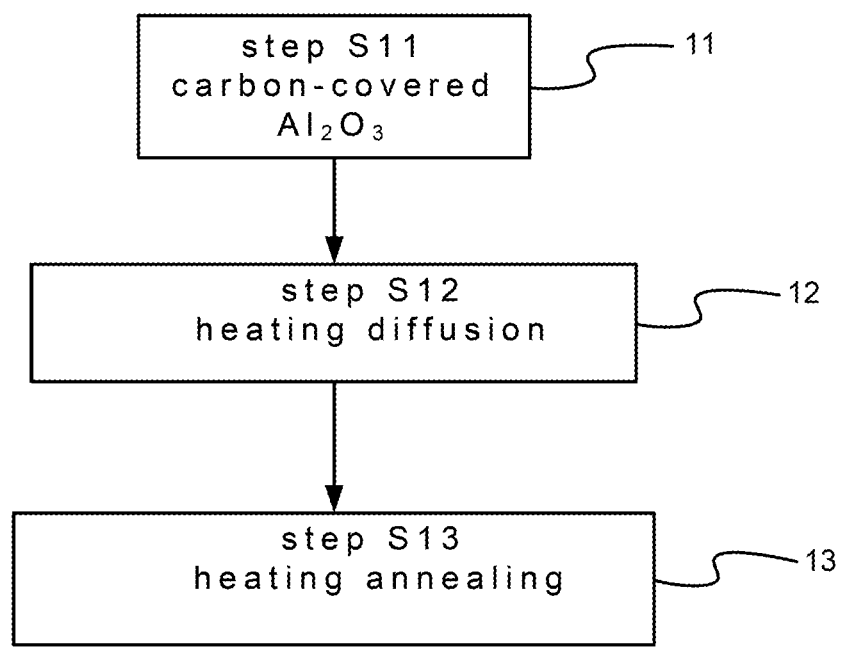

METHOD FOR PRODUCING OPTICALLY STIMULATED LUMINESCENE DOSAGE DETECTION CRYSTAL

FIELD OF THE INVENTION

The present invention relates to a method for producing an OSL dosage detection crystal; and more particularly to a method for producing the optically stimulated luminescene (OSL) dosage detection crystal associated with radiation dosimetry where an $Al_2O_3$ is first covered with carbon, and which is then has an in-vacuum diffusion and an ambient pressure annealing so that oxygen vacancy deficiencies are formed in the $Al_2O_3$ crystal.

DESCRIPTION OF THE RELATED ART

There is a demand for measuring an environmental and human body radiation dosage, and which is performed by basing on radiation dosimetry. And, the radiation dosimetry is conducted based on thermoluminescence (TL) and optically stimulated luminescene (OSL) characteristics of a material.

The TL is a mechanism where the material releases a light resulted from heat after absorbing a radiation energy. On the other hand, the OSL is a mechanism where the material releases a light owing to a light after absorbing the radiation energy.

In comparison with the TL, the OSL dosimetry has not a need to be heated in the use course, effectively avoiding a heat quench at its radiation center. Further, the OSL also has the advantages of a high sensitivity and a simple use.

However, the radiation dosimetry has long been ignored in some extent since it is aimed to the light emitting material having a high sensitivity of radiation, a high light emitting efficiency for the OSL cases, a smaller number of efficient atoms, and a better performance of light attenuation, which is rarely available as the best known in the art.

An $Al_2O_3$ crystal has a superior TL performance. Its growth methods include Czochralski, Cz and Kyropoulos, KY. Between them, the KY method may only grow a pure $Al_2O_3$. However, the pure $Al_2O_3$ crystal only has a low sensitivity for the TL. To improve the TL performance of the $Al_2O_3$ crystal, a research panel of Landauer successfully grew $\alpha$-$Al_2O_3$:C crystal (M. S. Akselrod et. al. Highly sensitive thermoluminescent anion-defective Ot-$Al_2O_3$:C single crystal detectors, Radiation Protection Dosimetry, 1990, 32:15-20 by using a Cz method in a condition of a strong restoration environment with presence of graphite. As indicated after a series of research, the $\alpha$-$Al_2O_3$:C crystal has the characteristics of a high sensitivity, a single TL peak and a moderate temperature, a low backing and a low dosage threshold, a wide rage of linear dosage response, a low speed of TL and OSL performance attenuation, a good repetitive use in the low dosage cases, a high sensitivity of radiation, and a high OSL efficiency. Hence, the $\alpha$-$Al_2O_3$:C crystal has an extreme potential for serving as a TL and OSL material.

However, the current $\alpha$-$Al_2O_3$:C crystal growth and dosimetry manufacture have been monopoly by this US company Landauer. Although the TL and OSL dosimetries for the $\alpha$-$Al_2O_3$:C crystal have been widely used in the western countries for environmental and human dosage monitoring use. However, the Cz method involves a complicated process, and thus carbon is non-uniformly distributed in the $Al_2O_3$ crystal, making it difficult in obtaining a consistent quality of the $\alpha$-$Al_2O_3$:C crystal. At the same time, the crystal growth art still requires some costly equipment, a long production period, and a high cost.

Local in Taiwan, the growth method for the $\alpha$-$Al_2O_3$:C crystal and the research and manufacturing for the associated dosimetry may be found with an edge-defined film-fed growth (EFG) method by Yang et al., Silicates Bulletin, 2008, 36(5): 678-682, Non-Organic Material Bulletin, 2009, 24(2): 255-258. In the manufacturing process, a heated graphite body is used, resulting in a relatively inferior quality of $\alpha$-$Al_2O_3$:C having carbon and carbonate adhering on its surface.

Therefore, the prior art $\alpha$-$Al_2O_3$:C manufacture still has to be improved to satisfy the requirement for general use.

SUMMARY OF THE INVENTION

It is, therefore, an object of the present invention to provide a method for simply producing an OSL dosage detection crystal C:$Al_2O_3$ structure having a uniform carbon distribution, so that the issues existing in the prior art may be effectively overcome.

It is a secondary object of the present invention to provide a C:$Al_2O_3$ detection crystal structure having a high sensitivity of optically stimulated luminescene (OSL) dosage response and a wide linear dosage response.

According to the present invention, the method for producing an OSL dosage detection crystal comprises steps of (a) coating a carbon film outside an $Al_2O_3$, so that a carbon in the carbon film covers the $Al_2O_3$ to form a carbon-covered $Al_2O_3$ structure; (b) placing the carbon-covered $Al_2O_3$ into a furnace, and subjecting the carbon-covered $Al_2O_3$ in the furnace to a diffusion process at a temperature of 1500° C. to 1900° C. in a vacuum oxygen-free environment so that carbon atoms in the carbon is diffused into $Al_2O_3$ lattices in the $Al_2O_3$; and (c) performing an annealing process in an open furnace at a pressure of 1 atm and a temperature of 1400° C. to 1800° C., so that the oxygen in the lattices within the $Al_2O_3$ reacts with the carbon to form a plurality of oxygen vacancy defects, whereby producing a C:$Al_2O_3$ structure.

In an embodiment, the carbon film is selected from graphite, $O_2$ powder, C-paper, artificial graphite powder and a combination thereof.

In an embodiment, in the step (b) the diffusion process is performed at the temperature for 10 min. to 2 hr.

In an embodiment, in the step (c) the annealing process is performed at the temperature for 10 min. to 2 hr.

BRIEF DESCRIPTION OF THE DRAWINGS

The present invention will be better understood from the following detailed descriptions of the preferred embodiments according to the present invention, taken in conjunction with the accompanying drawings, in which:

FIG. 1 is a flowchart illustrating a production process according to the present invention.

DESCRIPTION OF THE PREFERRED EMBODIMENTS

Referring to FIG. 1, which is a flowchart of a producing method according to the present invention. As shown, the method for producing an optically stimulated luminescene (OSL) dosage detection crystal is illustrated and comprises the following steps.

At first, a carbon material in, such as its film, powder, and paper forms, etc is covered outside an $Al_2O_3$ (S11), so that a carbon in the carbon film covers the $Al_2O_3$ to form a carbon-covered $Al_2O_3$ structure. The used carbon film is selected from graphite, $O_2$ powder, C-paper, artificial graphite powder and a combination thereof.

Then, the carbon-covered $Al_2O_3$ is placed into a furnace, and the carbon-covered $Al_2O_3$ in the furnace is subject to a diffusion process at a temperature of 1500° C. to 1900° C. in a vacuum oxygen-free environment (S12), so that carbon atoms in the carbon is diffused into $Al_2O_3$ lattices in the $Al_2O_3$.

Finally, an annealing process is performed in an open furnace at a pressure of 1 atm and a temperature of 1400° C. to 1800° C. (S13), so that the oxygen in the lattices within the $Al_2O_3$ reacts with the carbon to form a plurality of oxygen vacancy defects, whereby producing a $C:Al_2O_3$ detection crystal structure.

In this manner, the above disclosed process flow successfully constitutes a method for producing a novel OSL dosage detection crystal.

In essence, the method of the present invention first covers the $Al_2O_3$ with carbon. In vacuum, the carbon atoms are diffused into the $Al_2O_3$ lattices. Then, the annealing process is conducted under 1 atm so that the oxygen and carbon atoms react with each other. At this time, C+O result in CO, or C+$O_2$ form $CO_2$, so that oxygen vacancy deficiencies are formed in the $Al_2O_3$ crystal. At this rime, a uniformly carbon distributed crystal structure is thus simply obtained. This structure features a high sensitivity of OSL dosage detection and a wide range of linear dosage response.

In summary, the method of the present invention first covers the $Al_2O_3$ with carbon. The carbon atoms are then diffused into the $Al_2O_3$ lattices in vacuum. Then, the annealing process under 1 atm enables the oxygen and carbon atoms react with each other, so that oxygen vacancy deficiencies are formed in the $Al_2O_3$ crystal, whereby a uniformly carbon-distributed crystal structure is thus simply obtained.

From all these views, the present invention may be deemed as being more effective, practical, useful for the consumer's demand, and thus may meet with the requirements for a patent.

The above described is merely examples and preferred embodiments of the present invention, and not exemplified to intend to limit the present invention. Any modifications and changes without departing from the scope of the spirit of the present invention are deemed as within the scope of the present invention. The scope of the present invention is to be interpreted with the scope as defined in the claims.

What is claimed is:

1. A method for producing an optically stimulated luminescene (OSL) dosage detection crystal, comprising steps of:
   (a) coating a carbon film outside an $Al_2O_3$, so that a carbon in the carbon film covers the $Al_2O_3$ to form a carbon-covered $Al_2O_3$ structure;
   (b) placing the carbon-covered $Al_2O_3$ into a furnace, and subjecting the carbon-covered $Al_2O_3$ in the furnace to a diffusion process at a temperature of 1500° C. to 1900° C. in a vacuum oxygen-free environment so that carbon atoms in the carbon is diffused into $Al_2O_3$ lattices in the $Al_2O_3$; and
   (c) performing an annealing process in an open furnace at a pressure of 1 atm and a temperature of 1400° C. to 1800° C., so that the oxygen in the lattices within the $Al_2O_3$ reacts with the carbon to form a plurality of oxygen vacancy defects, whereby producing a $C:Al_2O_3$ structure.

2. The method as claimed in claim 1, wherein the carbon film is selected from graphite, $C_2$ powder, C-paper, artificial graphite powder and a combination thereof.

3. The method as claimed in claim 1, wherein in the step (b) the diffusion process is performed at the temperature for 10 min. to 2 hr.

4. The method as claimed in claim 1, wherein in the step (c) the annealing process is performed at the temperature for 10 min. to 2 hr.

* * * * *